(12) United States Patent
Takamatsu et al.

(10) Patent No.: US 9,512,067 B2
(45) Date of Patent: Dec. 6, 2016

(54) METHOD FOR PRODUCING XYLYLENE DIISOCYANATE AND SYSTEM FOR PRODUCING XYLYLENE DIISOCYANATE

(71) Applicant: MITSUI CHEMICALS, INC., Tokyo (JP)

(72) Inventors: Koji Takamatsu, Omuta (JP); Hideki Sone, Machida (JP); Masaaki Sasaki, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/781,703

(22) PCT Filed: Mar. 28, 2014

(86) PCT No.: PCT/JP2014/059307
§ 371 (c)(1),
(2) Date: Oct. 1, 2015

(87) PCT Pub. No.: WO2014/163017
PCT Pub. Date: Oct. 9, 2014

(65) Prior Publication Data
US 2016/0052875 A1   Feb. 25, 2016

(30) Foreign Application Priority Data

Apr. 3, 2013 (JP) ................................. 2013-077927

(51) Int. Cl.
| | |
|---|---|
| C07C 249/00 | (2006.01) |
| C07C 263/04 | (2006.01) |
| C07C 263/20 | (2006.01) |
| B01J 19/24 | (2006.01) |

(52) U.S. Cl.
CPC .............. *C07C 263/04* (2013.01); *B01J 19/24* (2013.01); *C07C 263/20* (2013.01); *B01J 2219/24* (2013.01)

(58) Field of Classification Search
CPC . C07C 263/04; C07C 265/14; C07C 263/20; B01J 19/24; B01J 2219/24
See application file for complete search history.

(56) References Cited

U.S. PATENT DOCUMENTS

| | | | | |
|---|---|---|---|---|
| 3,440,270 | A | * 4/1969 | McMaster | ............. C07C 263/00 560/339 |
| 5,196,572 | A | * 3/1993 | Okawa | ................... C07C 263/04 521/159 |
| 5,284,969 | A | 2/1994 | Hauner | |
| 5,386,053 | A | 1/1995 | Otterbach et al. | |
| 5,502,244 | A | * 3/1996 | Okawa | ................... C07C 263/04 560/345 |
| 2005/0043561 | A1 | 2/2005 | Michalczak | |
| 2011/0092731 | A1 | 4/2011 | Miyake | |
| 2012/0271067 | A1 | 10/2012 | Shimokawatoko et al. | |

FOREIGN PATENT DOCUMENTS

| | | |
|---|---|---|
| CN | 102652124 | 8/2012 |
| EP | 2147909 | 1/2010 |
| JP | 2231461 A2 | 9/1990 |
| JP | 4221356 A2 | 8/1992 |
| JP | 5255227 A2 | 10/1993 |
| JP | 7258194 A2 | 10/1995 |
| JP | 200568146 | 3/2005 |
| JP | 201363916 | 4/2013 |
| WO | 2009139062 A1 | 11/2009 |

OTHER PUBLICATIONS

Written opinion for International application JP2014/059307.*
International Search Report dated Jun. 24, 2014 filed in PCT/JP2014/059307.
International Preliminary Report on Patentability dated Oct. 15, 2015 filed in PCT/JP2014/059307.
Extended European Search Report dated Oct. 17, 2016 issued in the corresponding European patent application No. 147780712.

* cited by examiner

*Primary Examiner* — Yevegeny Valenrod
*Assistant Examiner* — Blaine G Doletski
(74) *Attorney, Agent, or Firm* — Rankin, Hill & Clark LLP (57) ABSTRACT

A method for producing xylylene diisocyanate includes a thermal decomposition step of thermally decomposing xylylene dicarbamate; a first separation step of separating, from the thermal decomposition product obtained in the thermal decomposition step, an isocyanate-containing component containing xylylene diisocyanate as a main component and an alcohol-containing component containing alcohol as a main component and containing xylylene diisocyanate as a subcomponent; a second separation step of separating xylylene dicarbamate and alcohol from the alcohol-containing component obtained in the first separation step; and a returning step of returning xylylene dicarbamate obtained in the second separation step to the thermal decomposition step.

2 Claims, 1 Drawing Sheet

METHOD FOR PRODUCING XYLYLENE DIISOCYANATE AND SYSTEM FOR PRODUCING XYLYLENE DIISOCYANATE

TECHNICAL FIELD

The present invention relates to a method for producing xylylene diisocyanate and a system for producing xylylene diisocyanate.

BACKGROUND ART

Diisocyanate is an organic compound having two isocyanate groups (—NCO), and is widely used industrially as a material for, for example, polyurethane and polyurea.

Conventionally, diisocyanate has been industrially produced by reaction (phosgene method) between amine and phosgene. However, phosgene has various problems such as being highly toxic and troublesome in handling, and requiring careful attention to corrosion of the equipment because it by-produces a large amount of hydrochloric acid. Accordingly, there is a need to develop industrial production methods for isocyanate that can replace the phosgene method.

Known diisocyanate production methods that do not use phosgene include a method (urea method) in which diamine, urea, and/or N-unsubstituted carbamic acid ester, and alcohol are allowed to react (carbamate-forming reaction), and the obtained N-unsubstituted carbamic acid ester (carbamate) is thermally decomposed to produce diisocyanate.

To be specific, for example, Patent Document 1 below has proposed a method for producing alicyclic diisocyanate in which, for example, alicyclic diamine, alcohol, and urea and/or urea derivative are allowed to react to synthesize diurethane; thereafter, the low boiling material, medium boiling material, and high boiling material are removed from the obtained diurethane, and furthermore, the alicyclic diurethane is thermally decomposed, and thereafter, alicyclic diisocyanate is separated, while reurethanzing a portion of the decomposed column bottom liquid with alcohol, recycling the reurethaniation product into the low boiling material separation.

CITATION LIST

Patent Document

Patent Document 1: Japanese Unexamined Patent Publication No. 2005-68146

SUMMARY OF THE INVENTION

Problem to be Solved by the Invention

However, there are disadvantages in that to produce xylylene diisocyanate in the same manner as in the above-described method of Patent Document 1, the yield of xylylene diisocyanate decreases.

That is, producing diisocyanate and alcohol by thermally decomposing diurethane (also called dicarbamate) in accordance with the method described in Patent Document 1 causes production of monoisocyanate (also called monourethane, monocarbamate) as its reaction intermediate.

Furthermore, because the above-described thermal decomposition is reversible reaction, and therefore recombination of diisocyanate and alcohol may cause production of monoisocyanate or diurethane.

The diurethane, monoisocyanate, and diisocyanate are usually in relation of equilibrium, but urethane compounds such as diurethane and monoisocyanate (monourethane) and isocyanate compounds such as diisocyanate and monoisocyanate may be reacted to form allophanate, and furthermore, the obtained allophanate may form isocyanurate.

Such formation of isocyanurate is irreversible reaction, and therefore the product (isocyanurate) of the isocyanurate formation is taken out as isocyanate residues (tar components), which may decrease the diisocyanate yield.

In this regard, xylylene diisocyanate, which is an aralkyl aliphatic diisocyanate, is disadvantageous in that xylylene diisocyanate easily forms allophanate compared with alicyclic diisocyanates.

Therefore, xylylene diisocyanate, xylylene dicarbamate, and xylylene monoisocyanate (monocarbamate) form allophanate as described above, and furthermore, the obtained allophanate forms isocyanurate: therefore, there are disadvantages in that a large amount of isocyanate residue (tar component) is caused, and the xylylene diisocyanate yield is decreased.

An object of the present invention is to provide a method for producing xylylene diisocyanate and a system for producing xylylene diisocyanate that allow for production of xylylene diisocyanate in high yield.

Means for Solving the Problem

To achieve the above object, a method for producing xylylene diisocyanate of the present invention includes
 a thermal decomposition step of thermally decomposing xylylene dicarbamate,
 a first separation step of separating, from the thermal decomposition product obtained in the thermal decomposition step,
   an isocyanate-containing component containing xylylene diisocyanate as a main component, and
   an alcohol-containing component containing alcohol as a main component and containing xylylene diisocyanate as a subcomponent,
 a second separation step of separating xylylene dicarbamate and alcohol from the alcohol-containing component obtained in the first separation step, and
 a returning step of returning xylylene dicarbamate obtained in the second separation step to the thermal decomposition step.

In the method for producing xylylene diisocyanate of the present invention, it is preferable that the alcohol-containing component has an alcohol content of 90 mass % or more relative to the total amount of the alcohol-containing component.

A system of producing xylylene diisocyanate of the present invention includes
 a thermal decomposition unit of thermally decomposing xylylene dicarbamate,
 a first separation unit of separating, from the thermal decomposition product obtained in the thermal decomposition unit,
   an isocyanate-containing component containing xylylene diisocyanate as a main component, and
   an alcohol-containing component containing alcohol as a main component and containing xylylene diisocyanate as a subcomponent,
 a second separation unit of separating xylylene dicarbamate and alcohol from the alcohol-containing component obtained in the first separation unit, and a returning unit of returning xylylene dicarbamate obtained in the second separation unit to the thermal decomposition unit.

In the system for producing xylylene diisocyanate of the present invention, it is preferable that the alcohol-containing component has an alcohol content of 90 mass % or more relative to the total amount of the alcohol-containing component.

Effect of the Invention

In a method for producing xylylene diisocyanate and a system of producing xylylene diisocyanate of the present invention, xylylene dicarbamate is thermally decomposed; and an isocyanate-containing component containing xylylene diisocyanate as a main component and an alcohol-containing component containing alcohol as a main component and containing xylylene diisocyanate as a subcomponent are separated from the obtained thermal decomposition product (first separation).

By performing separation so that xylylene diisocyanate is contained in the alcohol-containing component, mixing in of alcohol in the isocyanate-containing component can be suppressed. Therefore, the xylylene monoisocyanate content and the xylylene dicarbamate content in the isocyanate component can be decreased. Thus, side reactions such as allophanate formation can be suppressed, and decrease in isocyanate residue can be achieved.

Furthermore, in the method and system for producing xylylene diisocyanate of the present invention, xylylene dicarbamate and alcohol are separated from the alcohol-containing component (second separation), and the obtained xylylene dicarbamate is returned to be subjected to thermal decomposition. Therefore, xylylene dicarbamate can be efficiently used.

Thus, the method and system for producing xylylene diisocyanate of the present invention can improve the xylylene diisocyanate yield.

DESCRIPTION OF EMBODIMENTS

In the method for producing xylylene diisocyanate of the present invention, first, xylylene dicarbamate is thermally decomposed (thermal decomposition step).

Xylylene dicarbamate can be obtained by a known method without particular limitation. To be specific, for example, xylylene dicarbamate can be obtained by reaction between xylylenediamine, urea, and/or N-unsubstituted carbamic acid ester, and alcohol.

Examples of xylylenediamine include 1,3-xylylenediamine and 1,4-xylylenediamine, and they may be used singly, or may be used in combination.

N-unsubstituted carbamic acid ester is carbamic acid ester in which nitrogen atoms in the carbamoyl group are not replaced with functional groups (that is, nitrogen atom is bonded to two hydrogen atoms and one carbon atom), and for example, is represented by the general formula (1) below.

$$R^1O-CO-NH_2 \quad (1)$$

(where $R^1$ represents an alkyl group, or an aryl group that may have a substituent.)

In the above-described formula (1), examples of the alkyl group in $R^1$ include a linear or branched saturated hydrocarbon group having 1 to 8 carbon atoms including methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms including cyclohexyl and cyclododecyl.

The alkyl group in $R^1$ is preferably a linear or branched saturated hydrocarbon group having 1 to 8 carbon atoms, more preferably, a linear or branched saturated hydrocarbon group having 2 to 6 carbon atoms, even more preferably, a straight chain saturated hydrocarbon group having 2 to 6 carbon atoms.

In the above-described formula (1), examples of the N-unsubstituted carbamic acid ester in which $R^1$ is the alkyl group include saturated hydrocarbon N-unsubstituted carbamic acid esters such as methyl carbamate, ethyl carbamate, n-propyl carbamate, iso-propyl carbamate, n-butyl carbamate, iso-butyl carbamate, sec-butyl carbamate, tert-butyl carbamate, pentyl carbamate, hexyl carbamate, heptyl carbamate, octyl carbamate, iso-octyl carbamate, and 2-ethylhexyl carbamate; and alicyclic saturated hydrocarbon N-unsubstituted carbamic acid ester such as cyclohexyl carbamate and cyclododecyl carbamate.

In the above-described formula (1), examples of the aryl group that may have a substituent in $R^1$ include an aryl group having 6 to 18 carbon atoms such as phenyl, tolyl, xylyl, biphenyl, naphthyl, anthryl, and phenanthryl. Examples of the substituent include a hydroxyl group, a halogen atom (e.g., chlorine, fluorine, bromine, iodine, etc.), a cyano group, an amino group, a carboxyl group, an alkoxy group (e.g., alkoxy group having 1 to 4 carbon atoms such as methoxy, ethoxy, propoxy, butoxy, etc.), an aryloxy group (e.g., phenoxy group, etc.), an alkylthio group (e.g., alkylthio group having 1 to 4 carbon atoms such as methylthio, ethylthio, propylthio, butylthio, etc.) and an arylthio group (e.g., phenylthio group, etc.). When a plurality of the substituents are replaced with an aryl group, the substituents may be the same or different from each other.

In the above-described formula (1), examples of the N-unsubstituted carbamic acid ester in which $R^1$ is an aryl group that may have a substituent include aromatic hydrocarbon N-unsubstituted carbamic acid ester such as phenyl carbamate, tolyl carbamate, xylyl carbamate, biphenyl carbamate, naphthyl carbamate, anthryl carbamate, and phenanthryl carbamate.

These N-unsubstituted carbamic acid esters may be used singly or in a combination of two or more.

For the N-unsubstituted carbamic acid ester, preferably, N-unsubstituted carbamic acid ester in which $R^1$ is an alkyl group in the above-described formula (1) is used.

The N-unsubstituted carbamic acid ester used as the material component for the carbamate-forming reaction is described later in detail, but preferably, the N-unsubstituted carbamic acid ester used as the material component for the carbamate-forming reaction include those N-unsubstituted carbamic acid esters obtained by further separating from the low boiling component (described later) separated after carbamate-forming reaction.

Examples of the alcohol include primary to tertiary monohydric alcohol, and for example, is represented by the general formula (2) below.

$$R^1-OH \quad (2)$$

(where $R^1$ is the same as $R^1$ in the above-described formula (1).)

In the above-described formula (2), $R^1$ is the same as $R^1$ in the above-described formula (1), that is, represents an alkyl group or an aryl group that may have a substituent.

In the above-described formula (2), examples of the alcohol in which $R^1$ is the above-described alkyl group include linear or branched saturated hydrocarbon alcohols such as methanol, ethanol, n-propanol, iso-propanol, n-butanol (1-butanol), iso-butanol, sec-butanol, tert-butanol, pentanol, hexanol, heptanol, octanol, iso-octanol, and 2-ethylhexanol; and alicyclic saturated hydrocarbon alcohol such as cyclohexanol and cyclododecanol.

In the above-described formula (2), examples of the alcohol in which $R^1$ is the above-described aryl group that may have a substituent include phenol, hydroxytoluene, hydroxyxylene, biphenyl alcohol, naphthalenol, anthracenol, and phenanthrenol.

These alcohols may be used singly or in a combination of two or more.

For the alcohol, preferably, alcohol in which $R^1$ is an alkyl group in the above-described formula (2) is used, and more preferably, alcohol in which $R^1$ is an alkyl group having 1 to 8 carbon atoms is used, and even more preferably, alcohol in which $R^1$ is an alkyl group having 2 to 6 carbon atoms is used.

Furthermore, for the alcohol used as the material component for carbamate-forming reaction, preferably, alcohol that is by-produced when the N-unsubstituted carbamic acid ester is used as the material component in the carbamate-forming reaction (described later), and alcohol that is separated from the decomposition liquid obtained by thermal decomposition reaction of xylylene dicarbamate (described later) are used.

In this method, the above-described xylylenediamine, urea and/or N-unsubstituted carbamic acid ester, and alcohol are blended, and preferably, they are allowed to react in a liquid phase.

The mixing ratio between the xylylenediamine, urea and/or N-unsubstituted carbamic acid ester, and alcohol is not particularly limited, and can be selected suitably from a relatively wide range.

Usually, the amounts of urea and N-unsubstituted carbamic acid ester blended and the amount of the alcohol blended are in equal mol or more relative to the amino group of xylylenediamine, and thus the urea and/or the above-described N-unsubstituted carbamic acid ester and the alcohol themselves can also be used as a reaction solvent in this reaction.

When the urea and/or the above-described N-unsubstituted carbamic acid ester, and alcohol are used also as a reaction solvent, as necessary, an excessive amount of urea and/or the above-described N-unsubstituted carbamic acid ester or alcohol is/are used, but the when the excessive amount is large, the consumed energy in the separation step after the reaction increases, and therefore the overly excessive amount is not suitable in terms of industrial production.

Thus, the amounts of urea and/or the above-described N-unsubstituted carbamic acid ester blended are, in view of improving yield of xylylene dicarbamate, about 0.5 to 20 times mol, preferably 1 to 10 times mol, even more preferably 1 to 5 times mol relative to one amino group of xylylenediamine, and the amount of alcohol blended is about 0.5 to 100 times mol, preferably 1 to 20 times mol, even more preferably 1 to 10 times mol relative to one amino group of xylylenediamine.

In the reaction, the reaction solvent is not absolutely necessary, but for example, when the reaction material is solid or when the reaction product precipitates, for example, reaction solvents such as aliphatic hydrocarbons, aromatic hydrocarbons, ethers, nitriles, aliphatic halogenated hydrocarbons, amides, nitro compounds, N-methylpyrrolidinone, N,N-dimethylimidazolidinone, and dimethyl sulfoxide can be blended to improve operability.

The amount of the reaction solvent blended is not particularly limited, as long as the amount allows for dissolution of the target product, i.e., xylylene dicarbamate. However, industrially, the reaction solvent has to be recovered from the reaction solution, and therefore the energy consumed for the recovery is preferably decreased as much as possible, and a large amount of the reaction solvent decreases the reactant concentration to slow the reaction rate, and therefore preferably a small amount of the reaction solvent is used. To be more specific, the reaction solvent is used in the range of generally 0 to 500 parts by mass, preferably 0 to 100 parts by mass relative to 1 part by mass of xylylenediamine.

Furthermore, in this reaction, the reaction temperature is suitably selected in the range of, for example, 100° C. or more, preferably 150° C. or more, and for example, 350° C. or less, preferably 300° C. or less. The reaction temperature less than these may cause decrease in the reaction rate, whereas the reaction temperature more than these may cause increase in side reaction, which may cause decrease in the xylylene dicarbamate yield.

The reaction pressure is generally atmospheric pressure, but when the boiling point of the component in the reaction solution is lower than the reaction temperature, a pressure may be applied, and furthermore, as necessary a pressure can be reduced.

The reaction time is, for example, 0.1 hours or more, preferably 0.5 hours or more, and for example, 20 hours or less, preferably 10 hours or less. The reaction time shorter than these may reduce the xylylene dicarbamate yield. Meanwhile, the reaction time longer than these is inappropriate in terms of industrial production.

Furthermore, in this method, a catalyst can also be used.

The catalyst is not particularly limited, and examples thereof include tin (II) chloride, tin (IV) chloride, lead acetate, lead phosphate, antimony (III) chloride, antimony (V) chloride, aluminum acetylacetonate, aluminum-isobutyrate, aluminum trichloride, bismuth (III) chloride, copper (II) acetate, copper (II) sulfate, copper (II) nitrate, bis-(triphenyl-phosphine oxide)-copper (II) chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylate, cerium (IV) oxide, uranyl acetate, titanium tetraisopropanolate, titanium tetrabutanolate, titanium tetrachloride, titanium tetraphenolate, titanium naphthenate, vanadium (III) chloride, vanadium acetylacetonate, chromium (III) chloride, molybdenum (VI) oxide, molybdenum acetylacetonate, tungsten (VI) oxide, manganese (II) chloride, manganese (II) acetate, manganese (III) acetate, iron (II) acetate, iron (III) acetate, iron phosphate, iron oxalate, iron (III) chloride, iron (III) bromide, cobalt acetate, cobalt chloride, cobalt sulfate, cobalt naphthenate, nickel chloride, nickel acetate, and nickel naphthenatre.

Examples of the catalyst further include $Zn(OSO_2CF_3)_2$ (also shown as: $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts may be used singly or in a combination of two or more.

The catalyst is blended in an amount of, for example, 0.000001 to 0.1 mol, preferably 0.00005 to 0.05 mol relative to 1 mol of xylylenediamine. The amount of the catalyst larger than that will not further cause significant reaction acceleration effects, while the increase in the amount blended may increase costs. On the other hand, the amount of the catalyst smaller than that may not achieve reaction acceleration effects.

The catalyst may be added all at once, continuously, or dividedly and intermittently several times, any of which does not affect reaction activity, and is not limited.

Then, in the reaction, with the above-described conditions, for example, a reaction vessel is charged with xylylenediamine, urea and/or N-unsubstituted carbamic acid ester, alcohol, and as necessary a catalyst and a reaction solvent, and the mixture is stirred or mixed.

Xylylene dicarbamate is obtained in this manner as a main product.

In the reaction, ammonia is also by-produced.

When N-unsubstituted carbamic acid ester is blended in the reaction, for example, alcohol represented by the general formula (3) below is by-produced.

$$R^1\text{—OH} \tag{3}$$

(where $R^1$ is the same as $R^1$ in the above-described formula (1).)

In the reaction, for example, N-unsubstituted carbamic acid ester represented by the general formula (4) below is by-produced.

$$R^1O\text{—CO—NH}_2 \tag{4}$$

(where $R^1$ is the same as $R^1$ in the above-described formula (1).)

In this reaction, either of a batch reaction process or a continuous reaction process can be adopted.

Next, in this method, xylylene dicarbamate is separated from the obtained reaction solution by a known method, and at the same time, for example, excess (unreacted) urea and/or N-unsubstituted carbamic acid ester and excess (unreacted) alcohol; and the by-produced alcohol (the above formula (3)) and N-unsubstituted carbamic acid ester (the above formula (4)) are separated as low boiling components (light-boiling fractions).

Preferably, the alcohol (excess (unreacted) alcohol and by-produced alcohol) roughly separated from the low boiling components (light-boiling fractions) is used as a material component for the carbamate-forming reaction.

Therefore, the alcohol roughly separated from the low boiling components (light-boiling fractions) can be industrially effectively used.

Also, preferably, N-unsubstituted carbamic acid ester roughly separated from the low boiling components (light-boiling fractions) is used as a material component for the carbamate-forming reaction.

Therefore, the N-unsubstituted carbamic acid ester roughly separated from the low boiling components (light-boiling fractions) can be industrially effectively used.

Then, in this method, the xylylene dicarbamate obtained as described above is thermally decomposed, thereby producing xylylene diisocyanate (1,3-xylylene diisocyanate, 1,4-xylylene diisocyanate), and by producing alcohol represented by the general formula (5) below.

$$R^1\text{—OH} \tag{5}$$

(where $R^1$ is the same as $R^1$ in the above-described formula (1).)

The thermal decomposition is not particularly limited, and for example, any known decomposition method such as a liquid phase method or a vapor phase method can be used.

In the vapor phase method, the xylylene diisocyanate and alcohol obtained by the thermal decomposition can be separated from a gaseous product mixture by fractional condensation. In the liquid phase method, the xylylene diisocyanate and alcohol obtained by the thermal decomposition can be separated, for example, by distillation or using a solvent and/or inert gas as a support substance.

As the thermal decomposition, a liquid phase method is preferable from the viewpoint of workability.

In such method, the xylylene dicarbamate is thermally decomposed preferably in the presence of an inert solvent.

The inert solvent is not particularly limited as long as it dissolves at least the xylylene dicarbamate, is inert to the xylylene dicarbamate and the xylylene diisocyanate, and remains unreacted (i.e., stable) during the thermal decomposition. For efficient thermal decomposition reaction, the inert solvent preferably has a higher boiling point than the xylylene diisocyanate to be obtained.

The inert solvent is suitably selected in accordance with, for example, pressure conditions, and for example, aromatic hydrocarbons may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264-266° C.), triphenylmethane (boiling point: 358 to 359° C. (754 mmHg)), 1-phenylnaphthalene (boiling point: 324-325° C.), 2-phenylnaphthalene (boiling point: 357-358° C.), and biphenyl (boiling point: 255° C.), and dibenzyltoluene (boiling point: 391° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

The inert solvent also include esters (e.g., dioctyl phthalate, didecyl phthalate, didodecyl phthalate, etc.), and aliphatic hydrocarbons regularly used as a heating medium.

These examples of the inert solvent can be used singly or in a combination of two or more.

The inert solvent is blended in an amount in the range of 0.001 to 100 parts by mass, preferably 0.01 to 80 parts by mass, more preferably 0.1 to 50 parts by mass relative to 1 part by mass of xylylene dicarbamate.

In the thermal decomposition, for example, the inert solvent is blended in xylylene dicarbamate to thermally decompose xylylene dicarbamate, and thereafter, the inert solvent is separated and recovered, to be blended in xylylene dicarbamate again in thermal decomposition.

The reaction conditions for the thermal decomposition reaction are suitably set: for example, the thermal decomposition temperature of usually 350° C. or less, preferably 80 to 350° C., more preferably 100 to 300° C. The thermal decomposition temperature of lower than 80° C. may fail to achieve practical reaction rate, and furthermore, the thermal decomposition temperature of more than 350° C. may cause disadvantageous side reactions, such as polymerization of xylylene diisocyanate. The pressure at the time of thermal decomposition reaction is preferably a pressure that allows for vaporization of the obtained alcohol with the above-described thermal decomposition reaction temperature, and in terms of equipment and utilities, practically, the pressure at the time of thermal decomposition reaction is preferably 0.133 to 90 kPa.

In this method, as necessary, a catalyst can be further added.

The catalyst can be added at, although the timing can be different depending on the types of the catalyst, any time of the following: the time of the above-described reaction, before and after the distillation separation after the reaction, and before and after the separation of xylylene dicarbamate.

As the catalyst used in the thermal decomposition, one or more metal substance selected from Sn, Sb, Fe, Co, Ni, Cu, Cr, Ti, Pb, Mo, and Mn; or a metal compound such as oxide, halide, carboxylate, phosphate, and an organic metal compound of these used in urethane reaction between xylylene diisocyanate and hydroxyl groups is used. Of these examples of catalysts, because Fe, Sn, Co, Sb, and Mn exhibit effects of suppressing by-products, they are preferably used.

Examples of metal catalysts of Sn include tin oxide, tin chloride, tin bromide, tin iodide, tin formate, tin acetate, tin oxalate, tin octylate, tin stearate, tin oleate, tin phosphate, dibutyltin dichloride, dibutyltin dilaurate, and 1,1,3,3-tetrabutyl-1,3-dilauryloxydistannoxane.

Examples of metal catalysts of Fe, Co, Sb, and Mn include acetate, benzoate, naphthenate, and acetylacetonato salt thereof.

The blending amount of the catalyst (metal substance or a compound thereof) relative to the reaction liquid is in the range of 0.0001 to 5 mass %, preferably in the range of 0.001 to 1 mass %.

In the thermal decomposition reaction, as necessary, a stabilizer can also be blended.

Examples of the stabilizer include o-toluene sulfonamide and p-toluene sulfonamide, and they may be used singly or in a combination of two or more.

The mixing ratio of the stabilizer is not particularly limited, and is set suitably in accordance with the purpose and application.

The thermal decomposition reaction can be conducted in any of the batch reaction, in which xylylene dicarbamate, a catalyst, and an inert solvent are charged at once, and the continuous reaction, in which xylylene dicarbamate is charged in an inert solvent containing a catalyst under reduced pressure.

The conversion rate of xylylene dicarbamate in the thermal decomposition is, for example, 70 mol % or more, preferably 90 mol % or more. The conversion rate of xylylene diisocyanate is determined in conformity with Examples described later.

Meanwhile, in the above-described thermal decomposition step, two carbamate groups of xylylene dicarbamate are thermally decomposed to produce xylylene diisocyanate, and the thermal decomposition liquid may further contain, for example, xylylene monoisocyanate (xylylenemonocarbamate), or xylylene dicarbamate.

Then, those compounds having carbamate groups such as xylylene dicarbamate and xylylene monoisocyanate are allowed to react with a compound having an isocyanate group such as xylylene diisocyanate and xylylene monoisocyanate, which may cause, for example, allophanate formation and isocyanurate formation, thereby producing thermal decomposition residues (isocyanate residues (tar component)).

In this method, first, the high boiling component containing thermal decomposition residues and the inert solvent is separated from the low boiling component containing the above-described thermal decomposition product (xylylene diisocyanate and alcohol).

The separation method is not particularly limited, and a known distillation column may be used.

Then, from the high boiling component, as necessary, the inert solvent is separated so that thermal decomposition residues are obtained. The obtained thermal decomposition residues are stored, and then disposed of. As necessary, they can be reused by a known method. Furthermore, the separated inert solvent can be reused for thermal decomposition.

Meanwhile, the thermal decomposition product is separated into the liquid component containing xylylene diisocyanate and the gas component containing alcohol by distillation, and thereafter, the obtained xylylene diisocyanate is purified.

However, if xylylene diisocyanate is contaminated with alcohol at the time of xylylene diisocyanate purification, recombination of xylylene diisocyanate and alcohol may cause production of xylylene dicarbamate or xylylene monoisocyanate. Then, the mixed presence of xylylene dicarbamate or xylylene monoisocyanate along with xylylene diisocyanate may cause, as described above, reaction of a compound having a carbamate group such as the xylylene dicarbamate and xylylene monoisocyanate with a compound having an isocyanate group such as xylylene diisocyanate and xylylene monoisocyanate, thereby causing, for example, allophanate formation or isocyanurate formation, and producing purification residues (isocyanate residues (tar component)).

Thus, in this method, first, the isocyanate-containing component containing xylylene diisocyanate as a main component and the alcohol-containing component containing alcohol as a main component and containing xylylene diisocyanate as a subcomponent are separated from the above-described thermal decomposition product (first separation step).

To be more specific, in this method, for example, the above-described thermal decomposition product is first vaporized by, for example, a rectifying column to obtain a gaseous mixture of xylylene diisocyanate and alcohol. Thereafter, xylylene diisocyanate in the gaseous mixture is condensed by using a separator such as a condenser and xylylene diisocyanate is recovered as the liquid component, and alcohol is recovered as the gas component. Separation conditions (temperature, pressure, etc.) are suitably set so as not to mix alcohol in the isocyanate-containing component.

To be specific, when using a rectifying column to obtain the gaseous mixture of xylylene diisocyanate and alcohol, the column top temperature is, for example, 70° C. or more, preferably 90° C. or more, more preferably 110° C. or more, and for example, 250° C. or less, preferably 230° C. or less, more preferably 210° C. or less. The column bottom temperature is, for example, 100° C. or more, preferably 150° C. or more, and for example, 350° C. or less, preferably 300° C. or less. The residence time at the column bottom is, for example, 0.1 hour or more, preferably 0.5 hours or more, and for example, 20 hours or less, preferably 10 hours or less.

Furthermore, when using a condenser to condense xylylene diisocyanate in the gaseous mixture, the condensate temperature is, for example, 20° C. or more, preferably 40° C. or more, more preferably 60° C. or more, and for example, 200° C. or less, preferably 180° C. or less, more preferably 160° C. or less.

This causes xylylene diisocyanate to be mixed as a subcomponent in the alcohol-containing component.

At this time, xylylene diisocyanate and alcohol are recombined to obtain xylylene monoisocyanate, but the obtained xylylene monoisocyanate is contained in the isocyanate-containing component along with the xylylene diisocyanate.

The isocyanate-containing component has a xylylene diisocyanate (main component) content of, for example, 70 mass % or more, preferably 90 mass % or more relative to the total amount of the isocyanate-containing component excluding the solvent.

The xylylene diisocyanate yield in the isocyanate-containing component relative to the material xylylene dicarbamate is, for example, 70 mol % or more, preferably 90 mol % or more.

The xylylene monoisocyanate yield in the isocyanate-containing component relative to the material xylylene dicarbamate is, for example, 30 mol % or less, preferably 10 mol % or less.

The isocyanate-containing component has a xylylene diisocyanate content of, for example, 80 mol % or more, preferably 90 mol % or more relative to the total of xylylene diisocyanate and xylylene monoisocyanate. The isocyanate-containing component has a xylylene monoisocyanate content of, for example, 20 mol % or less, preferably 10 mol % or less relative to the total of xylylene diisocyanate and xylylene monoisocyanate.

The mixture of xylylene monoisocyanate and xylylene diisocyanate (isocyanate-containing component) obtained in the first separation step is purified by a known method. The purified xylylene diisocyanate is stored and reserved, for example, in a known storage tank. Meanwhile, when an isocyanate residue containing xylylene monoisocyanate (purification residue) is obtained, for example, it is stored and then disposed of. As necessary, it can also be reused by a known method.

By conducting the separation so that xylylene diisocyanate is contained in the alcohol-containing component in this manner, mixing in of alcohol in the isocyanate-containing component can be suppressed. Therefore, the xylylene monoisocyanate content and the xylylene dicarbamate content in the isocyanate component can be decreased. Thus, side reactions such as allophanate formation can be suppressed, and decrease in isocyanate residue can be achieved.

That is, for example, when the isocyanate component contains alcohol along with xylylene diisocyanate, recombination of xylylene diisocyanate and alcohol produces xylylene dicarbamate or xylylene monoisocyanate (monocarbamate). Therefore, in the isocyanate component, xylylene diisocyanate, xylylene dicarbamate, and xylylene monoisocyanate (monocarbamate) may react to cause allophanate formation, and also the obtained allophanate may undergo isocyanurate formation to produce isocyanate residue.

In contrast, when mixing in of alcohol in the isocyanate-containing component is suppressed, the xylylene dicarbamate content and the xylylene monoisocyanate content in the isocyanate component can be reduced. Therefore, reaction of xylylene dicarbamate, xylylene monoisocyanate (monocarbamate), and xylylene diisocyanate can be suppressed, and as a result, reduction of the isocyanate residue can be achieved.

Meanwhile, in the above-described first separation step, the alcohol-containing component (gas component) contains alcohol as a main component, and xylylene diisocyanate as a subcomponent.

The alcohol-containing component has an alcohol (main component) content of, for example, 90 mass % or more, preferably 95 mass % or more, and generally 99.99 mass % or less relative to the total amount of the alcohol-containing component excluding the solvent.

The alcohol-containing component has a xylylene diisocyanate (subcomponent) content of, for example, 10 mass % or less, preferably 5 mass % or less, and generally 0.01 mass % or more relative to the total amount of the alcohol-containing component excluding the solvent.

When the alcohol-containing component has the alcohol content and the xylylene diisocyanate content in the above-described range, mixing in of alcohol in the isocyanate-containing component can be suppressed quite excellently. Therefore, the xylylene monoisocyanate content and the xylylene dicarbamate content in the isocyanate component can be decreased. Thus, side reactions such as allophanate formation can be suppressed, and decrease in isocyanate residue can be achieved.

When the alcohol-containing component is cooled to condense, xylylene diisocyanate and alcohol mixedly present in the alcohol component are recombined to produce xylylene dicarbamate.

Thus, in this method, xylylene dicarbamate and alcohol are further separated from the alcohol-containing component obtained in the above-described first separation step (second separation step).

In the second separation step, for example, by using a separator such as a condenser, xylylene dicarbamate in the alcohol-containing component obtained in the above-described first separation step is condensed to be recovered as the liquid component, and alcohol is recovered as the gas component.

In this manner, xylylene dicarbamate and alcohol can be separated from the alcohol-containing component obtained in the first separation step.

Next, in this method, the xylylene dicarbamate obtained in the above-described second separation step is returned to the above-described thermal decomposition step, and subjected to thermal decomposition again (returning step).

To be more specific, for example, the xylylene dicarbamate obtained in the second separation step is purified as necessary, and is returned to a feed line for feeding xylylene dicarbamate to the thermal decomposition step, to be mixed with the material xylylene dicarbamate and used.

By returning the xylylene dicarbamate obtained in the second separation step to the thermally decomposing step, xylylene dicarbamate can be used efficiently, and the xylylene diisocyanate yield can be improved.

After the alcohol obtained in the second separation step is separated and recovered, the alcohol can be used, for example, as a material component of xylylene dicarbamate production.

Then, in the method for producing xylylene diisocyanate, as described above, xylylene dicarbamate is subjected to thermal decomposition, and from the obtained thermal decomposition product, the isocyanate-containing component containing xylylene diisocyanate as a main component and the alcohol-containing component containing alcohol as a main component are separated (first separation).

By conducting the separation so that xylylene diisocyanate is contained in the alcohol-containing component in this manner, mixing in of alcohol into the isocyanate-containing component can be suppressed. Therefore, the xylylene monoisocyanate content and the xylylene dicarbamate content in the isocyanate component can be decreased. Thus, side reactions such as allophanate formation can be suppressed, and decrease in isocyanate residue can be achieved.

In the method for producing xylylene diisocyanate, as described above, xylylene dicarbamate and alcohol are separated from the alcohol-containing component (second separation), and the obtained xylylene dicarbamate is returned to be subjected to thermal decomposition. Therefore, xylylene dicarbamate can be efficiently used.

Thus, the method for producing xylylene diisocyanate can improve the xylylene diisocyanate yield.

In the following, an embodiment of a plant in which the above-described method for producing xylylene diisocyanate is industrially conducted is described with reference to FIG. 1.

Figure 1:
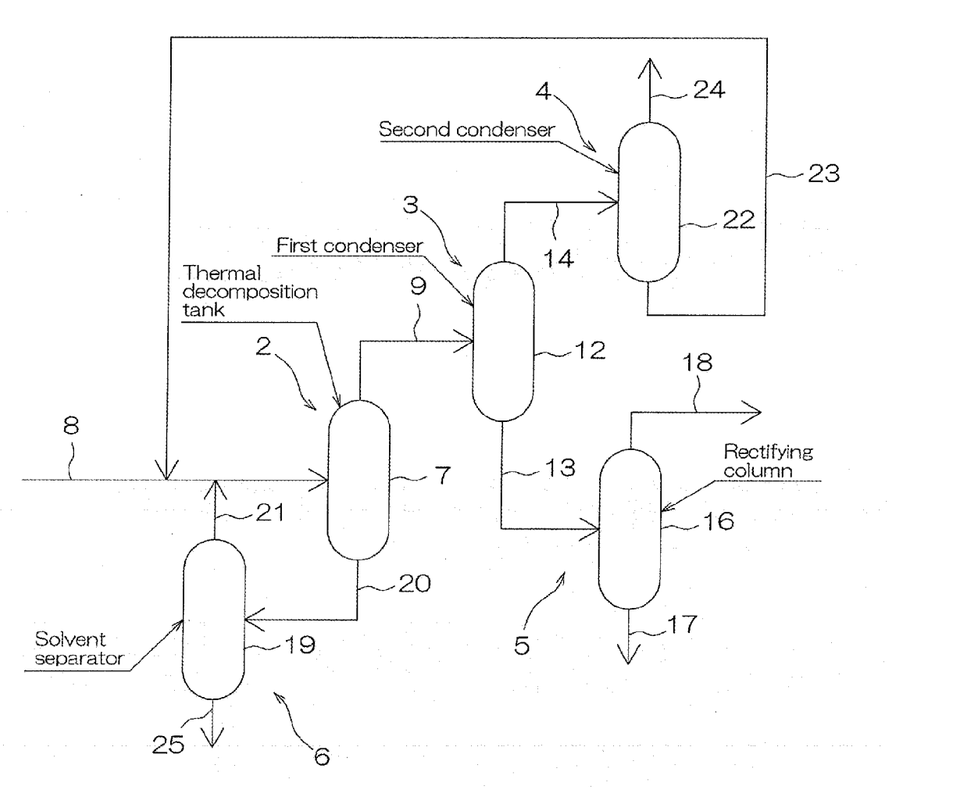
FIG. 1 is a schematic diagram illustrating an embodiment of a plant in which a method for producing xylylene diisocyanate of the present invention is used.

In FIG. 1, a plant 1 is a xylylene diisocyanate production system for producing xylylene diisocyanate from xylylene dicarbamate, and includes a thermal decomposition unit 2, a first separation unit 3, a second separation unit 4, a purification unit 5, and a solvent recovery unit 6.

The thermal decomposition unit 2 is provided in the plant 1 for thermal decomposition of xylylene dicarbamate into xylylene diisocyanate and alcohol.

The thermal decomposition unit 2 includes a thermal decomposition tank 7, and a carbamate feed pipe 8 and a thermal decomposition product transport pipe 9 connected to the thermal decomposition tank 7.

The thermal decomposition tank 7 is a decomposition tank in which xylylene dicarbamate is heated to thermally decompose into xylylene diisocyanate and alcohol, and is composed of a heat-resistant and pressure-resistant vessel capable of controlling temperatures and pressures. The thermal decomposition tank 7 is provided with, although not shown, as necessary, for example, a solvent feed pipe for feeding a solvent to the thermal decomposition tank 7.

To be specific, the thermal decomposition tank 7 is formed with, at its bottom, a decomposition chamber having a stirrer and at its top, a distillation chamber having a distillation column, and for example, the lower end portion of the distillation column of the distillation chamber is connected to the upper end portion of the decomposition chamber.

The carbamate feed pipe 8 is, for example, a carbamate transport line for transporting the mixture containing xylylene dicarbamate and an inert solvent into the thermal decomposition tank 7, and its downstream-side end portion is connected to a side portion of the thermal decomposition tank 7 at some position in the up-down direction. Although not shown, the upstream-side end portion of the carbamate feed pipe 8 is connected to, for example, a carbamate production system (not shown) for producing xylylene dicarbamate. In the carbamate production system (not shown), for example, as described above, xylylenediamine, urea and/or N-unsubstituted carbamic acid ester, and alcohol are allowed to react in the presence of an inert solvent to produce xylylene dicarbamate (urea method).

The thermal decomposition product transport pipe 9 is a thermal decomposition product transport line for transporting a mixture obtained by thermal decomposition of xylylene dicarbamate, to be specific, the thermal decomposition product containing xylylene diisocyanate and alcohol obtained by thermal decomposition reaction, and furthermore xylylene monoisocyanate and xylylene dicarbamate to the first separation unit 3 (described later), and its downstream-side end portion is connected to a side portion of the first condenser 12 (described later) of the first separation unit 3 at some position in the up-down direction. The upstream-side end portion of the thermal decomposition product transport pipe 9 is connected to, for example, a top portion of the distillation chamber (distillation column) of the thermal decomposition tank 7.

The first separation unit 3 is provided to separate, from the thermal decomposition product obtained in the thermal decomposition unit 2, the isocyanate-containing component containing xylylene diisocyanate as a main component, and the alcohol-containing component containing alcohol as a main component and containing xylylene diisocyanate as a subcomponent.

To be specific, the first separation unit 3 includes a first condenser 12, and a first condensate transport pipe 13 and a first vapor component transport pipe 14 connected to the first condenser 12.

The first condenser 12 is a separator for separating the above-described thermal decomposition product obtained in the thermal decomposition unit 2 into a first condensate (isocyanate-containing component) containing the xylylene diisocyanate as a main component, and a first vapor component (alcohol-containing component) containing alcohol as a main component, and is composed of a heat-resistant and pressure-resistant vessel capable of controlling temperatures and pressures.

Furthermore, although not shown, the first condenser 12 is provided with, for example, a pressure reduction means (vacuum pump, etc.) for reducing the pressure inside the first condenser 12, a temperature adjustment means (e.g., heater and cooler, etc.) for adjusting the temperature inside the first condenser 12, and a temperature sensor for administration of the temperature inside the first condenser 12.

The first condenser 12 is connected to the thermal decomposition unit 2 through the thermal decomposition product transport pipe 9 at the downstream side of the thermal decomposition unit 2.

The first condensate transport pipe 13 is a first condensate transport line for transporting the first condensate obtained in the first condenser 12 to the purification unit 5 (described later), and its upstream-side end portion is connected to the bottom portion of the first condenser 12. The downstream-side end portion of the first condensate transport pipe 13 is connected to a side portion of the rectifying column 16 at some position in the up-down direction.

The first vapor component transport pipe 14 is a first vapor component transport line for transporting the first vapor component obtained in the first condenser 12 to the second separation unit 4, and its upstream-side end portion is connected to the top portion of the first condenser 12. The downstream-side end portion of the first vapor component transport pipe 14 is connected to a side portion of the second condenser 22 (described later) of the second separation unit 4 at some position in the up-down direction.

The second separation unit 4 is provided for separating xylylene dicarbamate and alcohol from the first vapor component obtained in the first separation unit 3.

To be specific, the second separation unit 4 includes a second condenser 22, a second condensate return pipe 23 as a returning unit connected to the second condenser 22, and a second vapor component discharge pipe 24.

The second condenser 22 is a separator for separating the first vapor component obtained in the first condenser 12 into a second condensate containing xylylene dicarbamate, and a second vapor component containing alcohol; and is composed of a heat-resistant and pressure-resistant vessel capable of controlling temperatures and pressures.

Furthermore, although not shown, the second condenser 22 is provided with, for example, a pressure reduction means (vacuum pump, etc.) for reducing the pressure inside the second condenser 22, a temperature adjustment means (e.g., heater and cooler, etc.) for adjusting the temperature inside the second condenser 22, and a temperature sensor for administration of the temperature inside the second condenser 22.

The second condenser 22 is connected in series to the first condenser 12 at the downstream side of the first condenser 12 through the first vapor component transport pipe 14.

The second condensate return pipe 23 is a second condensate return line for returning the second condensate (that is, xylylene dicarbamate) obtained in the second condenser 22 to the thermal decomposition unit 2, and its upstream-side end portion is connected to the bottom portion of the second condenser 22. The downstream-side end portion of the second condensate return pipe 23 is connected to a some position of the carbamate feed pipe 8 of the thermal decomposition unit 2.

The second vapor component discharge pipe 24 is a second vapor component discharge line for taking out the second vapor component obtained in the second condenser 22 from the plant 1, and its upstream-side end portion is connected to the top portion of the second condenser 22. The downstream-side end portion of the second vapor component discharge pipe 24 is connected to, although not shown, for example, an alcohol condenser.

The purification unit 5 is provided to separate and purify, from the first condensate obtained in the first separation unit 3, xylylene diisocyanate and xylylene monoisocyanate.

The purification unit 5 includes a rectifying column 16, and a monoisocyanate-containing residue drain pipe 17 and a diisocyanate drain pipe 18 connected to the rectifying column 16.

The rectifying column 16 is a purification column for separating and purifying, from the first condensate obtained in the first separation unit 3, xylylene diisocyanate and xylylene monoisocyanate, and is composed of a known distillation column.

The monoisocyanate-containing residue drain pipe 17 is a purification residue drain line for draining the component remained after purifying xylylene diisocyanate in the rectifying column 16, to be specific, the purification residue containing xylylene monoisocyanate, and its upstream-side end portion is connected to the bottom portion of the rectifying column 16. The downstream-side end portion of the monoisocyanate-containing residue drain pipe 17 is connected, although not shown, to a purification residue storage tank in which the purification residue is stored.

The diisocyanate drain pipe 18 is a diisocyanate drain line for draining the xylylene diisocyanate separated and purified in the rectifying column 16 from the plant 1, and its upstream-side end portion is connected to the top portion of the rectifying column 16. The downstream-side end portion of the diisocyanate drain pipe 18 is connected to, although not shown, for example, an isocyanate storage tank.

The solvent recovery unit 6 is provided for separating and recovering the inert solvent from the mixture liquid (primary residue) of the inert solvent and the isocyanate residue obtained in the thermal decomposition unit 2.

The solvent recovery unit 6 includes a solvent separator 19, a residue transport pipe 20, a solvent return pipe 21, and a residue drain pipe 25.

The solvent separator 19 is a separator for separating the inert solvent from the mixture liquid (primary residue) of the inert solvent and the isocyanate residue obtained in the thermal decomposition unit 2, and composed, for example, of a known evaporator such as a thin film evaporator.

The solvent separator 19 is provided with, although not shown, a stirring means for stirring inside the solvent separator 19, a temperature adjustment means (e.g., heater and cooler, etc.) for adjusting the temperature of the solvent separator 19, and a temperature sensor for administration of the temperature inside the solvent separator 19.

The residue transport pipe 20 is a residue transportation line for transporting the mixture liquid (primary residue) of the inert solvent and the isocyanate residue obtained in the thermal decomposition unit 2 to the solvent separator 19, and its upstream-side end portion is connected to the bottom portion of the thermal decomposition tank 7. The downstream-side end portion of the residue transport pipe 20 is connected to a side portion of the solvent separator 19 at some position in the up-down direction.

The solvent return pipe 21 is a solvent return line for returning the inert solvent separated in the solvent separator 19 to the thermal decomposition unit 2, and its upstream-side end portion is connected to the top portion of the solvent separator 19. The downstream-side end portion of the solvent return pipe 21 is connected to some position of the carbamate feed pipe 8 of the thermal decomposition unit 2.

The residue drain pipe 25 is a secondary residue drain line for draining the component (secondary residue) remained after the inert solvent is separated from the primary residue in the solvent separator 19, and its upstream-side end portion is connected to the bottom portion of the solvent separator 19. The downstream-side end portion of the residue drain pipe 25 is connected to, although not shown, a secondary residue storage tank in which the secondary residue is stored.

Next, description is given below of a method for producing xylylene diisocyanate with the plant 1.

In this method, first, xylylene dicarbamate is transported by pressure to the thermal decomposition tank 7 of the thermal decomposition unit 2 through the carbamate feed pipe 8. Then, the thermal decomposition unit 2 is operated continuously so that xylylene dicarbamate is heated and thermally decomposed in the thermal decomposition tank 7 under the above-described conditions.

The thermal decomposition conditions include the following: a residence time of the fed material in the thermal decomposition tank 7 of, for example, 2 hours or more, preferably 4 hours or more, and for example, 20 hours or less, preferably 10 hours or less. The thermal decomposition temperature is, for example, 80° C. or more, preferably 100° C. or more, and for example, 350° C. or less, preferably 300° C. or less. The pressure is, for example, 0.133 kPa or more, and 90 kPa or less.

In this manner, a thermal decomposition product containing xylylene diisocyanate and alcohol is obtained as a decomposition liquid. At the same time, thermal decomposition residue is obtained.

The above-described thermal decomposition product obtained in the thermal decomposition tank 7 is introduced from the decomposition chamber to the distillation chamber, and introduced to the first condenser 12 of the first separation unit 3 as a gas component through the thermal decomposition product transport pipe 9.

In the first condenser 12, the above-described thermal decomposition product is condensed under the first separation conditions.

The first separation conditions, that is, the condensation conditions in the first condenser 12 are suitably set in accordance with the types of alcohol used and the pressure conditions. For example, when n-butanol is used, the temperature condition (first temperature) is, for example, more than 50° C., preferably 80° C. or more at 2.6 kPa.

To improve the xylylene diisocyanate yield, the temperature (first temperature) is preferably 100° C. or less, meanwhile, to improve purity of xylylene diisocyanate, the temperature (first temperature) is preferably 100° C. or more.

In this manner, the mixture obtained by the above-described thermal decomposition is separated into a first condensate (isocyanate-containing component) containing xylylene diisocyanate as a main component, and a first vapor component (alcohol-containing component) containing alcohol as a main component and xylylene diisocyanate as a subcomponent. The isocyanate-containing component contains xylylene monoisocyanate obtained by recombination of xylylene diisocyanate and alcohol.

The first condensate obtained in the first condenser 12 is transported to the rectifying column 16 of the purification unit 5 through the first condensate transport pipe 13, and in the rectifying column 16, xylylene diisocyanate and xylylene monoisocyanate are individually separated and purified.

The purified xylylene diisocyanate is drained through the diisocyanate drain pipe 18 from the plant 1. Then, the purified xylylene diisocyanate is transported to the isocyanate storage tank, which is not shown, and is stored in the isocyanate storage tank.

Meanwhile, the isocyanate residue (purification residue) contains xylylene monoisocyanate remained after purification of xylylene diisocyanate. The obtained isocyanate residue (purification residue) is drained through the monoisocyanate-containing residue drain pipe 17, and for example, stored, and then disposed of. As necessary, the obtained isocyanate residue (purification residue) can be reused by a known method.

The first vapor component obtained in the first condenser 12 is transported to the second condenser 22 of the second separation unit 4 through the first vapor component transport pipe 14.

In the first condenser 12, the first vapor component is condensed under the second separation conditions.

The second separation conditions, that is, the condensation conditions in the second condenser 22 are set suitably according to the types of alcohol used and the pressure conditions.

In the second condenser 22, xylylene diisocyanate and alcohol are recombined to obtain xylylene dicarbamate, and the obtained xylylene dicarbamate is obtained as a condensate. Meanwhile, alcohol is eliminated as a vapor component.

In this manner, the first vapor component is separated into a second condensate containing xylylene dicarbamate and a second vapor component containing alcohol.

Then, the second condensate obtained in the second condenser 22 is transported to some position of the carbamate feed pipe 8 through the second condensate return pipe 23, mixed with the material xylylene dicarbamate, and again fed to the thermal decomposition unit 2.

Meanwhile, the second vapor component obtained in the second condenser 22 is taken out through the second vapor component discharge pipe 24, introduced to, for example, an alcohol condenser which is not shown, and then the alcohol in the second vapor component is condensed and recovered. The recovered alcohol can be reused, for example, as a production material of xylylene dicarbamate.

In the plant 1, the mixture liquid (primary residue) of the inert solvent and the thermal decomposition residue obtained by thermally decomposing xylylene dicarbamate in the thermal decomposition tank 7 is transported to the solvent separator 19 through the residue transport pipe 20.

In the solvent separator 19, the mixture liquid of the inert solvent and the thermal decomposition residue is heated and distilled, and the inert solvent is separated. The separated inert solvent is returned to some position of the carbamate feed pipe 8 through the solvent return pipe 21, mixed with the material xylylene dicarbamate, and again fed to the thermal decomposition unit 2. The separation conditions for separating the inert solvent are not particularly limited, and are set suitably in accordance with the purpose and application.

Meanwhile, the component (secondary residue) remained after the inert solvent is separated from the primary residue is drained through the residue drain pipe 25 from the plant 1, disposed of, or stored and reused.

Then, in the plant 1, as described above, from the thermal decomposition product, the isocyanate-containing component containing xylylene diisocyanate as a main component and the alcohol-containing component containing alcohol as a main component and containing xylylene diisocyanate as a subcomponent are separated (first separation).

By conducting the separation so that the alcohol-containing component contains xylylene diisocyanate, mixing in of alcohol into the isocyanate-containing component can be suppressed. Therefore, the xylylene monoisocyanate content and the xylylene dicarbamate content in the isocyanate component can be decreased. Thus, side reactions such as allophanate formation can be suppressed, and decrease in isocyanate residue can be achieved.

Furthermore, in the plant 1, as described above, xylylene dicarbamate and alcohol are separated from the alcohol-containing component (second separation), and the obtained xylylene dicarbamate is returned to be subjected to thermal decomposition. Therefore, xylylene dicarbamate can be efficiently used.

Thus, in the plant 1, the xylylene diisocyanate yield can be improved.

Although the method and the system for producing xylylene diisocyanate are described above, the plant 1 may be provided with, as necessary, at suitable positions, a pre-treatment unit for conducting pre-treatment processes such as dehydration process, and a post-treatment unit for conducting post-treatment processes such as an intermediate process, a distillation process, a filtering process, a purification process, and a recovery process.

In the above-described plant 1, the thermal decomposition unit 2 and the first condensation unit 3 are individually described, but for example, a known rectifying column integrally including, for example, a thermal decomposition unit 2, a first condensation unit 3, and furthermore a second condensation unit 4 can be used, and also, the thermal decomposition residue (column bottom liquid) drained from the thermal decomposition tank 7, and a portion of the first condensate of the first condensation unit 3 can be returned into the thermal decomposition tank 7.

In the above-described plant 1, the downstream-side end portion of the second condensate return pipe 23 and of the solvent return pipe 21 is connected to some position of the carbamate feed pipe 8, but for example, the downstream-side end portion of the second condensate return pipe 23 and of the solvent return pipe 21 can be directly connected to, for example, the thermal decomposition tank 7.

EXAMPLES

In the following, the present invention is described in further detail with reference to Reference Examples, but the present invention is not limited in any way to Reference Examples. The values shown in Reference Examples below can be replaced with the corresponding values shown in embodiments (that is, upper limit value or lower limit value).

Reference Example 1

Xylylene dicarbamate and dibenzyltoluene as an inert solvent are mixed at a mass ratio of 1:1, thereby preparing a material component. Then, 100 ppm relative to xylylene dicarbamate of p-toluene sulfonamide as a stabilizer was added to the prepared material component.

Thereafter, the above-described material component was continuously fed to a 500 mL interior content glass-made four-neck flask equipped with a stirrer and a rectifying column having a return pipe at the top so that the feeding amount was 120 g/hr, and left there for 5 hours under the conditions of 255° C. and 3.33 kPa (25 torr). In this manner, the xylylene dicarbamate is thermally decomposed and a product containing xylylene diisocyanate and alcohol was obtained. The product contained xylylene monoisocyanate and xylylene dicarbamate.

Then, the product obtained by the above-described thermal decomposition was fed to a condenser having a temperature set to be 80° C. to be partially condensed to obtain a condensate, and the remainder was eliminated as a vapor component.

The xylylene dicarbamate conversion rate in the above-described thermal decomposition reaction determined by the following formula was 99 mol %.

The xylylene diisocyanate yield in the condensate determined by the following formula relative to the material xylylene dicarbamate was 93.7 mol %.

The xylylene monoisocyanate yield in the condensate determined by the following formula relative to the material xylylene dicarbamate was 3.2 mol %.

The xylylene dicarbamate yield in the vapor component determined by the following formula relative to the material xylylene dicarbamate was 0.1 mol %.

xylylene dicarbamate conversion rate=(amount of xylylene dicarbamate fed−amount of unreacted xylylene dicarbamate)÷amount of xylylene dicarbamate fed×100 xylylene diisocyanate yield in condensate=xylylene diisocyanate amount in isocyanate-containing component÷amount of xylylene dicarbamate fed×100 xylylene monoisocyanate yield in condensate=xylylene monoisocyanate amount in isocyanate-containing component÷amount of xylylene dicarbamate fed×100 xylylene dicarbamate yield in vapor component=xylylene dicarbamate amount in alcohol-containing component÷amount of xylylene dicarbamate fed×100

Reference Example 2

A condensate and a vapor component were obtained in the same manner as in Reference Example 1, except that the temperature in the condenser was set to 100° C.

The xylylene dicarbamate conversion rate in the above-described thermal decomposition reaction determined in the same manner as in Reference Example 1 was 99 mol %.

The xylylene diisocyanate yield in the condensate determined in the same manner as in Reference Example 1 relative to the material xylylene dicarbamate was 94.3 mol %.

The xylylene monoisocyanate yield in the condensate determined in the same manner as in Reference Example 1 relative to the material xylylene dicarbamate was 1.6 mol %.

The xylylene dicarbamate yield in the vapor component determined in the same manner as in Reference Example 1 relative to the material xylylene dicarbamate was 1.1 mol %.

Reference Comparative Example 1

A condensate and a vapor component were obtained in the same manner as in Reference Example 1, except that the temperature in the condenser was set to 70° C.

In the above-described thermal decomposition reaction, the xylylene dicarbamate conversion rate in the thermal decomposition reaction determined in the same manner as in Reference Example 1 was 99 mol %.

The xylylene diisocyanate yield in the condensate determined in the same manner as in Reference Example 1 relative to the material xylylene dicarbamate was 92.7 mol %.

The xylylene monoisocyanate yield in the condensate determined in the same manner as in Reference Example 1 relative to the material xylylene dicarbamate was 4.3 mol %.

The xylylene dicarbamate yield in the vapor component determined in the same manner as in Reference Example 1 relative to the material xylylene dicarbamate was 0.0 mol %.

The xylylene diisocyanate yields in the condensate in Reference Examples 1 to 2 and Reference Comparative Example 1 are shown in Table 1.

TABLE 1

| No | Thermal decomposition conditions | | | | Separation Conditions Temperature °C | Conversion Rate XDC mol % | Yield | | | | |
|---|---|---|---|---|---|---|---|---|---|---|---|
| | Amount Fed g/h | Residence time hr | Temperature °C | Pressure kPa | | | XDI mol % | XMI mol % | XDC mol % | XDI + XMI mol % | XDI + XMI + XDC mol % |
| Reference Example 1 | 120 | 5 | 255 | 3.33 | 80 | 99 | 93.7 | 3.2 | 0.1 | 96.9 | 97.0 |
| Reference Example 2 | 120 | 5 | 255 | 3.33 | 100 | 99 | 94.3 | 1.6 | 1.1 | 95.9 | 97.0 |
| Reference Comparative Example 1 | 120 | 5 | 255 | 3.33 | 70 | 99 | 92.7 | 4.3 | 0.0 | 97.0 | 97.0 |

The abbreviations in the Table are shown below.
XDC: xylylene dicarbamate
XDI: xylylene diisocyanate
XMI: xylylene monoisocyanate
From Table 1, it was confirmed that by thermally decomposing xylylene dicarbamate and then thereafter, separating the obtained condensate containing xylylene diisocyanate and xylylene monoisocyanate, and the vapor component containing xylylene dicarbamate and alcohol, the xylylene diisocyanate yield in the condensate improves.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

A method for producing xylylene diisocyanate and a system for producing xylylene diisocyanate of the present invention can produce xylylene diisocyanate with excellent yield, and therefore are used suitably for xylylene diisocyanate production, and in various industrial fields in which xylylene diisocyanate is used (e.g., isocyanate production, etc.).

DESCRIPTION OF REFERENCE NUMERALS

1 Plant
2 Thermal decomposition system
3 First separation unit
4 Second separation unit
23 Second condensate return pipe

The invention claimed is:

1. A method for producing xylylene diisocyanate comprising:
   a thermal decomposition step of thermally decomposing xylylene dicarbamate,
   a first separation step of separating, from the thermal decomposition product obtained in the thermal decomposition step,
      an isocyanate-containing component containing xylylene diisocyanate as a main component, and
      an alcohol-containing component containing alcohol as a main component and containing xylylene diisocyanate as a subcomponent,
   a second separation step of separating xylylene dicarbamate and alcohol from the alcohol-containing component obtained in the first separation step, and
   a returning step of returning xylylene dicarbamate obtained in the second separation step to the thermal decomposition step.

2. The method for producing xylylene diisocyanate according to claim 1, wherein the alcohol-containing component has an alcohol content of 90 mass % or more relative to the total amount of the alcohol-containing component.

* * * * *